United States Patent [19]

Mee et al.

[11] 4,224,031

[45] Sep. 23, 1980

[54] CI MASS SPECTROMETRIC ANALYSIS OF PHYSIOLOGICALLY ACTIVE COMPOUNDS

[76] Inventors: John M. L. Mee, 411 Opihikao Pl., Honolulu, Hi. 96825; Berthold Halpern, 88 Ramah Ave., Mt. Ousley, Australia, 2500; John Korth, Lot 66 O'Brien's Rd., Figtree, Australia, 2525

[21] Appl. No.: 851,666

[22] Filed: Nov. 15, 1977

[51] Int. Cl.[2] .......... G01N 33/16

[52] U.S. Cl. .......... 23/230 B

[58] Field of Search .......... 23/230 B, 230 M

[56] References Cited

PUBLICATIONS

Mee et al.-I, Analytical Letters, 9(12), 1075-1083 (1976).

Mee et al.-II, Analytical Letters, 9(6), 605-610 (1976.

Mee et al.-III, Biomed. Mass Spectrometry, 4:178 (1977).

Milne et al., Anal. Chem. 43, 1815 (1971).

Lundeen et al., Anal. Chem. 45, 1288 (1973).

Milne et al., Anal. Chem. 45, 1952 (1973).

Chas et al., Anal. Chem. 46, 296 (1974).

*Primary Examiner*—Arnold Turk

*Attorney, Agent, or Firm*—Bertram I. Rowland

[57] ABSTRACT

A method for determining an analyte is provided, wherein a sample is prepared in a form useful for chemical inonization mass spectrometry and analyzed. Included in the sample is an analog of the compound which differs in having an unnatural isotopic distribution. The combined analyte and analog are derivatized as appropriate and then subjected to chemical protonation in the gaseous phase to provide charged species. The resulting charged species are then analyzed mass spectrometrically and the amount of analyte is determined by determining the ratio of one or more of the major peaks of the analyte and its analog.

The method finds particular use in the determination of physiologically active compounds as found in physiological fluids, particularly blood. With blood, the analyte is extracted with an appropriate extraction solvent freed of protein, combined with its isotopically different analog, and the mixture then derivatized, if necessary. The analyte and analog or derivatives thereof are then subjected to chemical protonation in the vapor phase and the resulting charged species analyzed by mass spectrometry. By comparing the ratio of one or more major peaks of the analyte and analog, the amount of analyte may be determined.

9 Claims, No Drawings

CI MASS SPECTROMETRIC ANALYSIS OF PHYSIOLOGICALLY ACTIVE COMPOUNDS

BACKGROUND OF THE INVENTION

1. Field of the Invention

There is a continuing need for the rapid determination of various compounds, particularly those associated with the determination of diseased states, therapy, drug abuse and the like. Methods which are desirable require accuracy, sensitivity, and ease of handling. Numerous techniques have been employed for analysis, such as ion exchange, paper, thin layer and gas chromatography, and gas chromatography mass spectrometry.

2. Brief Description of the Prior Art

Mee, et al, Anal. Letters 9(12), 1075 (1976) reports a rapid and quantitative blood analysis for free fatty acids by chemical ionization mass spectrometry. Mee, et al, Biomed. Mass Spectrometry 4:178 (1977) reports the rapid and quantitative blood amino acid analysis by chemical ionization mass spectrometry. Mee and Halpern, Anal. Letters 9, 605 (1976) report the derivitization of amino acids for gas chromatography.

SUMMARY OF THE INVENTION

A wide variety of analytes, particularly those of physiological interest, are analyzed by chemical ionization mass spectrometry. In employing a physiological fluid, blood, for example, the analyte is extracted with an appropriate solvent from the blood and freed of protein. Included in the sample, either by treatment of the host or by addition is an isotopically labeled analog of the analyte; the mixture may be derivatized in preparing the sample for analysis. The analog differs from the analyte solely by having an unnatural isotopic composition. Conveniently, the analog may be deuterated or have an unnatural amount of isotopes of carbon, nitrogen or sulfur, so that the mass of the analog differs from the analyte. The analyte and analog or derivatives thereof are then volatilized and protonated in the gas phase to form charged species. The charged species are then subjected to mass spectrometric analysis and the amount of analyte determined by a comparison of major peaks, e.g. parent or first fragmentation peaks.

DESCRIPTION OF THE SPECIFIC EMBODIMENTS

A method is provided for analyzing for a wide variety of physiologically active compounds by employing chemical ionization mass spectrometry. Where the analyte of interest is derived from a physiological fluid, the analyte is extracted from the fluid by employing an appropriate solvent which preferentially extracts the analyte of interest. The analyte is freed of interfering materials and combined with an analog which differs from the analyte in having an unnatural isotopic composition.

Depending upon the analyte of interest, the analyte and analog are then derivatized to a volatilizable derivative and volatilized. The gaseous analyte and analog are then subjected to chemical protonation employing a proton transfer agent so as to form charged species. The charged species are then analyzed by mass spectrometrical analysis and by comparison of the ratio of major mass peaks of the analyte and the analog, the amount of analyte may be quantitatively determined.

The subject method finds particular use with the determination of compounds of physiological interest in blood. Illustrative of such compounds are amino acids, fatty acids, cholesteryl compounds e.g. cholesterol and cholesteryl fatty acid esters, and estrogens e.g. estriol.

In analyzing blood samples, microsamples may be employed which can be conveniently prepared and transported as dry blood spots on an absorbent paper e.g. filter paper disks. Generally, the blood sample may range from about 1 to 50, more usually from about 5 to 25 μl, which may be impregnated on the disk. Employing the disk has not only the advantage of convenience, but provides a means for retaining protein, while the compound or compounds of interest are extracted from the blood. Besides blood, urine, saliva, amniotic fluid, ocular lens fluid and the like may be analyzed.

The sample, either impregnated in a disk, or a fluid or a powder, is extracted with an appropriate solvent. The solvents will vary depending on the compound of interest. The less polar the analyte of interest, the less polar the solvent. The choice of solvent is not critical to the invention, in that it is evaporated prior to the analysis by chemical ionization mass spectrometry. Furthermore, the literature has extensive lists of solvents which have been employed for preferential extraction of analytes from various physiological fluids.

Illustrative extraction solvents include water, methanol, ethanol, chloroform, acetone, dimethylsulfoxide, mixtures thereof, and the like. The volume of solvent employed will depend upon the size of the sample, the amount of analyte which is involved, the solubility of the analyte, the solubility of interfering substances in the solvent, and the like. The amount chosen will normally be governed by the means of handling and ability to extract the compound of interest. Conveniently, the solvent and sample may be ultrasonically mixed to insure the effective transfer of the analyte to the solvent and the solution isolated.

Depending upon the analyte and solvent involved, the solution may be used directly in the next step or the solvent evaporated and the residue redissolved. With some analytes, no derivatization is required, with other analytes, derivatization is optional, and with a third group of analytes, derivatization is mandatory.

When one is determining lipids, the free fatty acids need not be derivatized and may be analyzed directly. By contrast, steroidal lipids e.g. cholesterol and estrogens, may optionally be derivatized. The derivatized compounds will normally be fatty acid esters, particularly saturated fatty acid esters of from 2 to 20 carbon atoms, more usualy of from 2 to 18 carbon atoms, and preferably of from 12 to 18 carbon atoms. The acids may be saturated or unsaturated, usually saturated, either straight chain or branched chain, normally straight chain.

The amino acids will normally be acylated to form amides and esterified with alkanols of from 1 to 6 carbon atoms, more usually of from 1 to 3 carbon atoms and preferably of 1 carbon atom. Illustrative alcohols include methanol, ethanol and propanol. The amines will be acylated with lower alkanoic or perfluoro lower alkanoic acids of from 1 to 6 carbon atoms, more usually of from 2 to 6 carbon atoms, and preferably of from 2 to 3 carbon atoms. The acylating agent may be acyl halide or anhydride, preferably the anhydride.

Particularly useful for amino acids is the combination of acetic anhydride and methanol. The sample containing the analyte is combined with a methanolic solution of acetic anhydride at a temperature in the range of 35° to 150° C., preferaby 80° to 100° C. for about 5 to 10 minutes, usually with agitation. At least stoichiometric amounts of the methanol and acetic anhydride are employed, the reaction requiring two moles of the anhydride.

Usually, solutions of amino acids of from 10 to 100 nanomoles or dry blood spots containing 5 to 10 μl of blood require from about 5 to 100 μl of acetic anhydride and from about 5 to 100 μl of methanol. Specifically a 5 μl blood spot will be mixed with 10 μl of acetic anhydride and 50 μl of methanol.

Acylating reagents of interest include acetic anhydride, propionic anhydride, butyric anhydride, trimethylacetic anhydride, trifluoroacetic anhydride, pentafluoropropionic anhydride, heptafluorobutyric anhydride, etc.

While other derivatizing agents may also be used for the amino acids, it is found that they are not as general as the derivatizing agents indicated above and to that extent are less practical and are not preferred. For example, the amino acid phenylalanine can be converted to an enamine ester with pivaldehyde as its trimethylanilinium or tetramethylammonium salt, which upon subsequent prolysis forms the neopentylidene enamine derivative as the methyl ester. However, enamine formation is slow and the pyrolysis inconvenient. Therefore, derivatization will normally occur by combining an alkanol and an anhydride with the amino acid at an elevated temperature for a short period of time.

Included in the same sample prior to derivatization or analysis is an analog of the analyte which differs solely from the analyte in having an unnatural average mass. That is, the analog has an unnatural amount of one or more rare isotopes. Among the isotopes which may be included are deuterium, tritium, carbon-13, carbon-14, nitrogen-15, and the like. Most conveniently, deuterium may be used. The analog will differ from the analyte by at least one mass number, preferably at least two mass numbers, and generally from about 2 to 6 mass numbers. The particular difference in mass is not significant, but is rather one of convenience of synthesis or commercial availability.

The amount of the analog which is employed may be varied widely, generally being not less than 0.01 mole ratio to the lowest concentration of the analyte range of interest and not greater than about 10 times the maximum number of moles of the range of interest.

The analysis may be carried out for a single compound or a mixture of compounds within a particular family or even a mixture of compounds from different families. Particularly, the analysis can be for a group of amino acids or fatty acids of interest or for one or more steriods or combinations thereof.

After the sample has been prepared, which is a combination of the analyte and its isotopically different analog or the derivatives thereof, an appropriately sized sample is introduced into a probe tip sample holder and evaporated in vacuo. The sample holder is then introduced into the mass spectrometer using a heatable direct insertion probe. The sample is volatilized and subjected to gas phase protonation employing an ionized hydrocarbon, normally of from 1 to 4 carbon atoms, particularly isobutane. It is found with isobutane, that a low level of fragmentation is obtained with intense parent peaks.

The protonated analyte and analog are then subjected to mass spectrometric analysis. Major peaks of varying heights are obtained of the analyte of interest and its isotopically different analog. Either the parent peak or a first fragmentation peak will normally be employed for determining ratios of peak heights. By carrying out standards having known amounts of the analyte of interest, a plot can be obtained of height ratios of the analyte and analog in relation to concentration of analyte.

The subject method provides an extremely sensitive and accurate technique for determining extremely low concentration or extremely small amounts of a wide variety of organic compounds of physiological interest. The method is sensitive to picogram amounts and provides a high degree of reproducibility and accuracy. Experience has shown that there is little if any interference by other compounds, where the appropriate choice of extractant solvent has been employed. Possible interferents are normally either insoluble in the extraction solvent or not sufficienly volatile for direct mass spectrometry.

As a practical convenience, standards can be provided for one or more compounds of the same class e.g. fatty acids, amino acids, steriods, etc., where two or more, usually three or more members of the class having unnatural isotopic compositions (usually having a mass number from 2 to 6 greater than the naturally occurring mass) are combined in proportionate ratios relating to the concentration ranges expected to be encountered in vivo. For example, for screening of fatty acids, a mixture of the even numbered saturated fatty acids would have a mole ratio of 1:1-30:1-150:1-50 for $C_{12}$:$C_{14}$:$C_{16}$:$C_{18}$ fatty acids respectively.

For amino acids, a similar mixture can be prepared. Conveniently, equal amounts of the isotopically unnatural amino acids may be employed or ratios reflecting average distribution can be employed. All of the naturally occurring amino acids can be determined, except that leucine and isoleucine cannot be distinguished.

EXPERIMENTAL

The following examples are offered by way of illustration and not by way of limitation. (All temperatures not otherwise indicated are centigrade. All percents not otherwise indicated are by weight).

EXAMPLE 1. ANALYSIS FOR CHOLESTEROL

Materials and Methods [2,2,3,4—$^2H_4$] Cholesterol (Prepared in accordance with the method of Diekman and Djerassi, J. Org. Chem., 32, 1005 (1967)

$\Delta^4$-cholesten-3-one (200 mg), tert-butanol-OD (7 ml) and potassium tert-butoxide (500 mg) were stirred under nitrogen for 3 hours. The solution was cooled and acidified with a mixture of acetic acid (OD) and deuterium oxide, extracted with methylene chloride and the organic layer washed with water, dried ($MgSO_4$) and evaporated. The mixture of $\Delta^4$- and $\Delta^5$-cholesten-3-ones (approx. 1:1) was separated by t.l.c. ($SiO_2$; ethyl acetate/60°-80° petroleum ether (1:4). The zone corresponding to $\Delta^4$-cholesten-3-one (90 mg), isopropenyl acetate (1.0 ml) and sulfuric acid —$D_2$ (10 μl) was then refluxed for 20 min. Sodium acetate (50 mg) was added to the solution and the solvent removed in vacuo. The solid residue was washed with chloroform (3×, 5 ml) and the washings decanted and evaporated. The residue (90 mg) was taken up in methanol and the solution stirred at room temperature while adding sodium borodeuteride (100 mg in 5 ml methanol). The solution was refluxed for 30 min, cooled and hydrochloric acid (3 ml, 2 N) was added dropwise. After extraction with ethyl acetate the organic layer was washed with water, dried and evaporated and the product crystallised from methanol (30 mg, mp 143°–146°). Mass spectrometric analysis showed that the material was identical to cholesterol labelled with one to five atoms of deuterium. It was calculated that the composition by moles was as follows: mono-deuterated molecules, 4%, dideuterated molecules, 12%, trideuterated molecules 24%; tetradeuterated molecules, 32%, pentadeuterated molecules, 28%.

[2,2,3,4-$^2H_4$] cholesteryl esters

Recrystallised stearic acid (20 mg) in benzene (2 ml) and pyridine (1 drop) was cooled to 0° and treated with oxalyl chloride (200 μl dropwise). Gas was evolved and the solution was allowed to warm to room temperature after which the solvent was removed in vacuo. Successive portions of benzene (2 ml ) were added and evaporated and the residue was redisolved in warm toluene (2 ml) and treated with [2,2,3,4,-$^2H_4$] cholesterol (5 mg) in benzene with 2 drops pyridine present. Pyridine hydrochloride crystallised slowly and the solution was left to stand at room temperature overnight. The solution was diluted with ether and washed with water, sodium carbonate solution, hydrochloric acid (1 N) and water, dried ($MgSO_4$) and evaporated. The residue was crystallised from acetone (5 mg, m.p. 68°–71°). [2,2,3,4-$^2H_4$]. Cholesteryl palmitate (5 mg, m.p. 76°–77°) was prepared in an identical manner using recrystallised palmitic acid.

Preparation of samples for mass spectrometry.

(a) Preparation of calibration samples.

Solutions containing 10–400 mg per 100 ml of cholesterol or cholesteryl palmitate were prepared by dissolving 0.5–2 μg in chloroform (5 μl). These were transferred in turn to a micro-vial and a solution of [2,2,3,4-$^2H_4$] cholesterol [5 μg] or its palmitate ester in chloroform [5 μl] was added. After sonication for 5 min, an aliquot of the solution was transferred to a probe tip sample holder, evaporated under vacuum and admitted to the mass spectrometer. The blood calibration samples were prepared by pipetting the spiked blood solutions onto filter paper, drying at 70° and then using procedure (b).

(b) Preparation of samples for free and total cholesterol determinations.

To a reaction vial were added chloroform-methanol (200 μl, 2:1 v/v), [2,2,3,4-$^2H_4$] cholesterol (5 μg in 5 μl chloroform) and the dry blood spot (filter paper disc, 4 mm diameter containing 5 μl). The vial was capped and the contents ultrasonically mixed for 5 min. The filter paper disc, which retains the denatured protein and other chloroform-methanol insolubles was removed with tweezers and the solution evaporated to dryness with nitrogen at 80°. The dry residue was dissolved in hexane (25 μ) and an aliquot (10 μl) was transferred to a probe tip sample holder, evaporated under vacuum and admitted to the mass spectrometer. The remainder of the hexane solution (15 μl) was evaporated to dryness and the residue was redissolved in a methanolic solution of sodium methoxide (0.5 N, 50 μl). The vial was capped and the contents were heated at 100° for 15 min. The solution was then evaporated to dryness, redissolved in hexane (15 μl) and an aliquot (10 μl) transferred to a probe tip for mass spectrometric analysis.

(c) Preparation of samples for free and esterified cholesterol determinations.

To a reaction vial were added chloroform-methanol (200 μl, 2:1 v/v), [2,2,3,4-$^2H_4$] cholesterol (5 μg in 5 μl chloroform) and its palmitate esters (5 μg in 5 μl chloroform) and the dry blood spot (filter paper disc, 4 mm diameter containing 5 μl). The vial was capped and the contents ultrasonically mixed for 5 min. The filter paper disc was then removed with tweezers and the solution concentrated down to about 25–30 μl with nitrogen at 80°. An aliquot (10 μl) was transferred to a probe tip sample holder, evaporated under vacuum and admitted to the mass spectrometer for free and esterified cholesterol determinations by temperature programmed mass spectrometry.

Mass Spectrometry

The mass spectra were recorded on a Dupont 21-491B mass spectrometer modified for operation in the chemical ionization mode. The reagent gas used was isobutane at pressures between 0.5 to 1.0 Torr. The source temperature was maintained at 200°. The energy of the electron beam was 70 eV. The block voltage was 1400 VDC and the repeller plates were maintained at the block voltage. Mass spectra for free cholesterol were recorded at 140°–160° with a background spectrum being taken at 50°. Mass spectra of esterified cholesterol were recorded at solid probe temperatures of 250°–270°. The concentrations of the cholesterol in the samples were determined by comparing the average spectral line intensity of [2,2,3,4-$^2H_4$] cholesterol at m/e 373 with that of the unlabelled cholesterol at m/e 369 and averaging the results from 10 measurements.

Results

The chemical ionization mass spectrum of cholesterol is dominated by a large ion at m/e 369, which is due to the loss of water from the protonated molecular ion at m/e 387. A quantitative analysis of cholesterol could be made by a direct comparison of the intensities of this ion and that of the corresponding ion at m/e 373 derived from a known amount of [2,2,3,4-$^2H_4$] cholesterol standard. A calibration curve was established from ion intensity measurements of a concentration range of cholesterol solutions and a graphical analysis of the data confirmed the linearity of the assay. The calibration curve was also confirmed using cholesterol enriched blood, corresponding to cholesterol concentrations of 10–400 mg per 100 ml. Since the specificity of the method is based on the assumption that there are no contaminants in the extract which contribute ions at m/e 369 and 373, part of the extracts from 5 blood samples were analysed either by mass spectrometry or after purification by thin-layer chromatography. The purified extracts gave the same ratio between 369 and 373 as did the original extracts indicating that prior purification was unnecessary. The specificity was further tested by using the protonated molecular ions of cholesterol and [2,2,3,4-$^2H_4$] cholesterol at m/e 387 and m/e 391 for the quantitation instead of the ions at m/e 369 and m/e 373. The results obtained with these ions were identical with those obtained previously. The effect of the presence of cholestryl esters in the blood on the assay for free cholesterol was established by adding chromatographically pure samples of cholesteryl palmitate and stearate to the blood prior to extraction. The ion intensities at m/e 369 and m/e 373 of the extract were not changed by the addition of the esters provided the recordings were made at a solid probe temperature of 150°±10°. At higher temperatures (>250° C.) cholesteryl palmitate and stearate are volatilized into the ion source and the spectral recordings yield the ion at m/e 369 (back peak) and the protonated molecular ions of the corresponding $C_{16:0}$ and $C_{18:0}$ fatty acid at m/e 257 and 285. Linear calibration curves for cholesteryl palmitate and stearate were established from the ion intensities at m/e 369 and m/e 373 at 250° using [2,2,3,4-$^2H_4$] cholesteryl palmitate and stearate as internal standards. These calibrations were also repeated using cholesterol and cholesteryl esters enriched blood.

Finally free and total cholesterol levels of a number of microsamples of blood dried on filter paper were determined at 150° and 250° probe temperatures using [2,2,3,4-$^2H_4$] cholesterol and its palmitate esters as internal standards. The relative standard deviation of the method as calculated from five independent analyses of the same blood (n=18) was found to be 0.64% for free cholesterol (31–76 mg%) and 1.08% for total cholesterol (100–296 mg%). Total cholesterol values were also compared with results obtained by the Calbiochem enzymatic cholesterol method (Table 1) and with the values obtained from a mass spectrometric analysis of the corresponding totally saponified blood samples (Table 2).

TABLE 1

COMPARISON OF THE MASS SPECTROMETRIC METHOD AND THE CALBIOCHEM ENZYMATIC METHOD FOR DETERMINATION OF TOTAL CHOLESTEROL.

| | Total Cholesterol (mg %)[(a)] | | |
|---|---|---|---|
| Sample | Mass Spectrometry | | Calbiochem Enzymatic Cholesterol (on corresponding) serum |
| 1 | 219.2 | 222.3 | 221.8 |
| 2 | 238.5 | 236.1 | 242.1 |
| 3 | 240.5 | 238.6 | 234.7 |
| 4 | 100.1 | 101.7 | 99.9 |
| 5 | 224.1 | 226.5 | 227.8 |
| 6 | 243.6 | 246.3 | 252.5 |

[(a)]Each value represents the mean of two independent determinations of the same sample.

TABLE 2

COMPARISON OF THE DIRECT MASS SPECTROMETRIC ANALYSIS OF BLOOD AND SAPONIFIED BLOOD FOR THE DETERMINATION OF TOTAL CHOLESTEROL.

| | Cholesterol (mg %)[(a)] | | | |
|---|---|---|---|---|
| Sample | Free | Esterified | Total[(b)] (calculated) | Total (saponified blood) |
| 1 | 58.3 | 92.1 | 150.4 | 148.6 |
| 2 | 66.8 | 131.9 | 198.7 | 196.5 |
| 3 | 55.4 | 80.7 | 136.1 | 135.5 |
| 4 | 75.3 | 119.6 | 194.9 | 195.2 |
| 5 | 61.2 | 142.9 | 204.1 | 202.7 |

[(a)]Each value represents the mean of two independent determinations of the same sample.
[(b)]Total = Free + Esterified

EXAMPLE 2. ANALYSIS OF AMINO ACIDS

The following is the general procedure for preparation and derivatization of a dry blood sample for determination of amino acids.

To a reaction vial were added ethanol (200 μl, 80% v/v) labeled amino acid standard ca 12 nmol and the dry blood spot (filter paper disk, 4 mm diameter containing ca 5 μl blood). The vial was capped and the contents ultrasonically mixed for 5 min. The filter paper disk, which retains the denatured protein, was removed with tweezers and the solution evaporated to dryness with nitrogen at 80°. The dry residue was then derivatized.

A solution of the above amino acids (10–100 nanomol) in 0.1 N HCl is prepared and transferred to a microreaction vial (0.5 ml capacity) and the appropriate amino acid or amino acid mixture labelled with either deuterium or nitrogen-15 added. The solution was then evaporated to dryness under a stream of nitrogen at 80°. The residue was redissolved in a mixture of acetic anhydride (10 μl) and anhydrous methanol (50 μl) and molecular sieve (type 3A, 1 stick) was added. The vial was capped and the contents ultrasonically mixed for 2 min. After heating at 100° for 5 min., an aliquot of the solution (approximately 10 μl) was transferred to a probe tip sample holder, evaporated in vacuo and admitted to the mass spectrometer using a heatable direct insertion.

A calibration curve was prepared employing deuterated phenylalanine, which was commercially available having a mixture of varying degrees of deuteration, but solely employing the pentadeuterated peak for analysis and augmenting blood with varying amounts of phenylalanine. Employing this curve, samples of blood from varying individuals were analyzed for phenylalanine. The following table indicates the results.

The mass spectra were recorded on a Dupont 21-191 B mass spectrometer modified for operation in the chemical ionization (c.i. mode). The reagent gas used was isobutane at a pressure between 0.5–1.0 Torr. The source temperature was maintained at 200° and the probe temperature was varied from ambient to 200°. The energy of the electron beam was 70 eV. The block voltage was 1400 VDC. and the repeller plates were maintained at the block voltage. Mass spectra were recorded at 50° intervals from 50° to 300° with a background spectrum being recorded at 50°. The concentrations of the individual amino acids were determined by comparing the average spectral line intensity of the labeled amino acid with that of the corresponding unlabeled amino acid and averaging the results from at least 5 measurements.

TABLE 3

Phenylalanine analyses of phenylketonuric blood and plasma by mass spectrometry and ion exchange chromatography

| Patient | Mass Spectrometry (blood spot) concentration mg % | Mean ± s.e.m.[a] mg % | Ion exchange (plasma) mean[b] mg % |
|---|---|---|---|
| G.L. | 18.24 | | |
| | 18.10 | | |
| | 18.68 | 18.48 ± 0.30 | 18.81 |
| | 18.53 | | |
| | 18.83 | | |
| F.T. | 20.89 | | |
| | 20.60 | | |
| | 20.45 | 20.60 ± 0.25 | 20.30 |
| | 20.74 | | |
| | 20.30 | | |
| W.M. | 14.86 | | |
| | 15.16 | | |
| | 15.01 | 14.98 ± 0.29 | 15.80 |
| | 14.57 | | |
| | 15.30 | | |
| S.S. | 12.80 | | |
| | 13.39 | | |
| | 13.09 | 13.09 ± 0.24 | 13.04 |
| | 12.95 | | |
| | 13.24 | | |

[a]s.e.m. = standard error of mean.
[b]Average of two analyses.

Calibration curves were then prepared for a number of selected amino acids using either commercially available deuterated amino acids or amino acids having nitrogen-15 or preparing such derivatives. After preparing appropriate calibration plots and determining the mean peak height ratios, a commercially available amino acids mixture containing 1 nanomol per 1 μl of each of the amino acids indicated in the following table was analyzed. The following table indicates the results.

TABLE 4.

Amino Acid Analysis by c.i. Mass Spectrometry.

| Amino Acid | Amino Acid Mixture (1nmol/μl) Mean[a] ± | S.E.M.[b] |
|---|---|---|
| Gly | 1.04 | 0.02 |
| Val | 1.00 | 0.01 |
| Asp | 1.06 | 0.02 |
| Glu | 1.04 | 0.02 |
| Phe | 0.96 | 0.01 |
| Tyr | 1.03 | 0.02 |

[a]Average of 4 analyses
[b]S.E.M. = Standard Error of Mean

Experiments were carried out further by repeating the calibration on artificially prepared blood spot amino acid solutions. Linearity of the assay was confirmed for glycine, valine, and phenylalanine respectively for a concentration range of 0 to 15 nanomol.

The above described technique was then employed for the determination of amino acids in saliva and amniotic fluid. The following table indicates the results.

TABLE 5

Physiological Amino Acids Levels of Saliva and Amniotic Fluid. Normal adult and pregnant subjects (pooled sample of 5) used for the complete procedure.

| Amino Acid | SALIVA mg % | C.V. | AMNIOTIC FLUID mg % | C.V. |
|---|---|---|---|---|
| Glycine | 0.67[a] (0.5-3.6)* | 2.3[b] | 1.11[a] (0.9-1.3)** | 2.5[b] |
| Valine | 1.33 (0.7-2.2) | 1.9 | 0.72 (0.5-2.3) | 2.1 |
| Aspartic acid | 0.37 (0.35-1.3) | 2.1 | 0.50 (—) | 2.0 |
| Glutamic acid | 0.64 (0.5-1.3) | 1.9 | 1.21 (1.1-3.3) | 1.8 |
| Phenylalanine | 0.62 (0.6-2.5) | 1.7 | 0.68 (0.3-1.2) | 1.9 |
| Tyrosine | 0.52 (0.2-1.0) | 1.9 | 0.47 (0.3-1.3) | 1.8 |

[a]Average of 5 spectral analysis
[b]C.V. = Coefficient of variation
*Altman & Dittmer (ed.) in Metabolism, p. 239, Fed. of Am. Soc. for Experimental Biology, Bethesda, Md.
**O'Neill et al, Obst. Gyn. 37, 550 (1971).

EXAMPLE 3. ANALYSIS FOR FREE FATTY ACIDS

Methods and Materials

Preparation of α-Deuterated Fatty Acids

Deuterium labeled fatty acids were prepared by a modification of van Heyningen's technique (van Heyningen et al, Biol. Chem. 125, 495 (1938)). A standard solution of fatty acid (0.2 mg of $C_{12:0}$ to $C_{18:0}$ or phytanic acid) in chloroform (0.2 ml) was transferred to a screw top reaction vial (ca 2 ml) and the solvent removed with nitrogen. Acetic anhydride-$D_6$ (100 μl), $D_2O$ (100 μl) and conc. $D_2SO_4$ (25 μl) were then added, the vial capped and heated at 150°-160° for 20 hr. The vial was then cooled and vented. The labeled fatty acids were extracted into hexane (400 μl), washed with $H_2O$ (400 μl) and dried. Deuterium incorporation was determined by mass spectroscopy and the fatty acids showed a minimum isotopic purity of 86% D in the two α-positions.

Chemical-Ionization Mass Spectrometric Analysis

Mass spectra were recorded as described above. The concentrations of the individual fatty acids were determined by comparing the peak height of the protonated molecular ion of the labeled fatty acid with that of the corresponding unlabeled acid and the results averaged from five measurements.

Preparation and Analysis of a Dried Blood Sample

To a reaction vial was added a chloroform-methanol mixture (500 μl, 2:1 v/v), the appropriate deuterium labeled fatty acid standard (ca. 1-2 g), and the dry blood spot (9 mm filter paper disc, ca. 20 μl blood). The mixture was then ultrasonically mixed for 5 min, the filter paper disk retaining the protein and other chloroform-methanol insoluble components, was removed with tweezers and the solution evaporated to dryness with nitrogen at 80°. The dry residue was then redissolved in chloroform (25 μl), ca. 10 μl transferred to a probe tip, evaporated under vacuum and admitted to the mass spectrometer via the solid probe.

Results

Experiments with individual free fatty acids showed they could be readily detected by C.I. mass spectrometry. The C.I. mass spectra of the saturated and the unsaturated free fatty acids were dominated by large protonated molecular ion peaks ($[MH]^+$) and unique m/e values were obtained for fatty acids $C_{12:0}$ to $C_{20:0}$ (Table 6). A quantitative analysis was made by comparison of the $[MH]^+$ of the fatty acids with that of the corresponding labeled fatty acid standards. By using fixed amounts of deuterated fatty acids ($D_2$) as internal standards calibration curves for the fatty acids ($C_{12:0}$, $C_{14:0}$, $C_{16:0}$, $C_{18:0}$) were determined for a particular concentration range.

TABLE 6

C.I. mass spectral data for fatty acids.

| Fatty Acid | $[MH]^+$ | Fatty Acid | $[MH]^+$ |
|---|---|---|---|
| $C_{12:0}$ | 201 | $C_{18:0}$ | 285 |
| $C_{14:0}$ | 229 | $C_{18:1}$ | 283 |
| $C_{15:0}$ | 243 | $C_{18:2}$ | 281 |
| $C_{16:0}$ | 257 | $C_{18:3}$ | 279 |
| $C_{16:1}$ | 255 | $C_{20:0}$ | 313 |

Graphical analysis of the data confirmed the linearity of the assay. The calibration curves were used to calculate chemical and isotopic correction factors. The linearity of the assay was also confirmed for an artificially prepared blood sample supplemented with different amounts of stearic acid. This method was then used to analyze a prepared fatty acid mixture and the concentration of each fatty acid calculated. The results were in excellent agreement with values obtained by G.C. analysis (Table 7).

TABLE 7

Analysis of fatty acid mixture by C.I. mass spectrometry and chromatography.

| Fatty Acid | Mass Spectrometry w/w %[1] | S.D.[2] | Gas Chromatography w/w %[1] | S.D.[2] |
|---|---|---|---|---|
| $C_{12:0}$ | 18.66 | 0.56 | 18.41 | 0.64 |
| $C_{14:0}$ | 17.91 | 0.52 | 18.11 | 0.62 |
| $C_{16:0}$ | 35.45 | 0.96 | 35.80 | 1.10 |
| $C_{18:0}$ | 27.99 | 0.78 | 27.68 | 1.02 |

[1]Average of 5 determinations
[2]Standard Deviation

The technique was then employed to determine the free fatty acid components of blood but since suitably labeled unsaturated acid standards were not available only the saturated free fatty acids were quantitated (Table 8).

TABLE 8

Analysis of blood spots by C.I. mass spectrometry.

| Fatty Acid(1) | Patient A mg %(2) | Patient A S.D.(3) | Patient B mg %(2) | Patient B S.D.(3) |
|---|---|---|---|---|
| $C_{12:0}$ | 0.24 | 0.01 | 0.39 | 0.01 |
| $C_{14:0}$ | 2.00 | 0.06 | 2.15 | 0.05 |
| $C_{16:0}$ | 10.44 | 0.29 | 8.69 | 0.25 |
| $C_{18:0}$ | 3.48 | 0.09 | 3.04 | 0.08 |

(1)Plasma free fatty acids have been determined by gas chromatography. The literature suggests that the levels are from 1.0–2.8 mg % ($C_{14:0}$), 0.4–11.3 mg % ($C_{16:0}$) and 0.2–3.9 mg % ($C_{18:0}$).
(2)Average of 5 determinations.
(3)Standard Deviation.

C.I. mass spectrometry permits the determination of all common free fatty acids in blood down to a level of 25 ng at a signal/noise ratio better than 10:1.

As demonstrated by the above data, the subject method provides for a rapid, accurate analysis of a wide variety of physiologically interesting compounds. Conventional extraction techniques can be employed to optimize the isolation of the compounds of interest. When necessary, compounds such as amino acids may be readily derivatized to volatile compounds. Isotopically different analogs of the compounds of interest can be readily prepared to provide internal standards. By employing internal standards, the method is not dependent upon accurate transfers of volumes or even complete transfers. So long as homogeneity of the sample is maintained, once the internal standard is measured and added, the method is relatively free of operator error. In addition, the method can be readily automated, so as to minimize subjective error.

Also, a number of compounds can be analyzed simultaneously, without interfering with each other, rather than requiring individual determinations.

Although the foregoing invention has been described in some detail by way of illustration and example for purposes of clarity of understanding, it will be obvious that certain changes and modifications may be practiced within the scope of the appended claims.

What is claimed is:

1. A method for quantitatively determining at least one analyte in blood, wherein the blood sample is a dried spot on absorbent paper, which comprises:

extracting said analyte with an extraction solvent from said paper, while leaving blood proteins bound to said paper;

including with said analyte an analog of the same composition of said analog but differing in mass, wherein said analog is present in at least from 0.01 moles per mole of the lowest concentration of the analyte in the range of interest and not more than ten times the maximum concentration of the analyte in the range of interest;

simultaneously derivatizing said analyte and analog to provide a volatizable product, when said analyte is not readily volatizable;

vaporizing said analyte and analog or the derivatives thereof and protonating them in the gaseous phase with a charged proton transfer agent to form chemically protonated analyte and analog or derivatives thereof;

subjecting said chemically protonated analyte and analog or derivatives thereof to mass spectrometric separation; and determining the amount of said analyte by comparison of a ratio of peak heights of the protonated analyte and analog.

2. A method according to claim 1, wherein said analyte is at least one amino acid and said derivatizing comprises:

combining said amino acid with a methanolic solution of acetic anhydride at a temperature in the range of 35° to 150° C. for a time sufficient to convert said amino acid to the acetamide and methyl ester.

3. A method according to claim 1, wherein said analyte is at least one fatty acid of from 12 to 20 carbon atoms.

4. A method according to claim 1, wherein said extraction solvent is a chloroform-methanol mixture and said analyte is a lipid.

5. A method according to claim 1, wherein said extraction solvent is ethanolic and said analyte is an amino acid.

6. A method according to claim 1, wherein said proton transfer agent is isobutane.

7. A method according to claim 1, wherein said analyte is at least one steroid.

8. A method according to claim 7, wherein said steroid is cholesterol or its fatty acid ester.

9. A method according to claim 7, wherein said steroid is an estrogen.

* * * * *